(12) United States Patent
Bock et al.

(10) Patent No.: US 11,570,880 B2
(45) Date of Patent: Jan. 31, 2023

(54) ISOCHRONOUS CYCLOTRONS EMPLOYING MAGNETIC FIELD CONCENTRATING OR GUIDING SECTORS

(71) Applicants: Varian Medical Systems Particle Therapy GmbH., Troisdorf (DE); Joachim Bock, Erftstadt (DE)

(72) Inventors: Joachim Bock, Erftstadt (DE); Arno Godeke, Bonn (DE)

(73) Assignee: Varian Medical Systems Particle Therapy GmbH, Troisdorf (DE)

( * ) Notice: Subject to any disclaimer, the term of this patent is extended or adjusted under 35 U.S.C. 154(b) by 0 days.

(21) Appl. No.: 16/838,750

(22) Filed: Apr. 2, 2020

(65) Prior Publication Data
US 2021/0315091 A1 Oct. 7, 2021

(51) Int. Cl.
| H05H 7/04 | (2006.01) |
| H01F 6/06 | (2006.01) |
| H05H 7/02 | (2006.01) |
| H05H 13/00 | (2006.01) |

(52) U.S. Cl.
CPC ............... *H05H 7/04* (2013.01); *H01F 6/06* (2013.01); *H05H 7/02* (2013.01); *H05H 13/005* (2013.01); *H05H 2007/025* (2013.01)

(58) Field of Classification Search
None
See application file for complete search history.

(56) References Cited

U.S. PATENT DOCUMENTS

| 10,383,206 | B1* | 8/2019 | Nuttens | ............... H05H 13/00 |
| 2007/0171015 | A1* | 7/2007 | Antaya | ............... H05H 7/04 |
| | | | | 335/216 |
| 2012/0126726 | A1* | 5/2012 | Antaya | ............... H05H 13/005 |
| | | | | 315/502 |
| 2013/0009571 | A1* | 1/2013 | Antaya | ............... H05H 13/005 |
| | | | | 315/502 |

(Continued)

FOREIGN PATENT DOCUMENTS

| JP | 2011258427 | 12/2011 |
| JP | 2015079626 | 4/2015 |
| WO | 2012030970 | 3/2012 |

OTHER PUBLICATIONS

Qin et al. Comparison of Beam Optics for Normal-Conducting and Superconducting Gantry Beamline Applied to the Proton Therapy System. Institute of Applied Electromagnetic Engineering. Huazhong University of Science and Technology (HUST). CPO-10, Key West, FL, USA, Oct. 19, 2018.

(Continued)

*Primary Examiner* — Crystal L Hammond

(57) ABSTRACT

An isochronous cyclotron including one or more coils and a plurality of pairs of bulk superconductor sectors. The one or more coils can be configured to generate a magnetic field in the beam chamber having a magnetic flux density that increases radially from the central axis of the beam chamber, and is orientated substantially perpendicular to the median acceleration plane of the beam chamber. Each pair of bulk superconductor sectors can be disposed on opposite sides of the median acceleration plane. The plurality of pairs of bulk superconductor sectors can be configured to guide or concentrate the magnetic field to provide an axial focusing component of the magnetic field.

25 Claims, 9 Drawing Sheets

(56) References Cited

U.S. PATENT DOCUMENTS

| | | | |
|---|---|---|---|
| 2013/0249443 | A1 | 9/2013 | Antaya et al. |
| 2014/0055058 | A1 | 2/2014 | Johnstone |
| 2014/0087953 | A1* | 3/2014 | Bromberg ............ H05H 13/005 |
| | | | 505/200 |
| 2014/0296075 | A1 | 10/2014 | Jongen et al. |
| 2014/0371076 | A1 | 12/2014 | Jongen |
| 2016/0353562 | A1 | 12/2016 | Antaya |
| 2016/0381780 | A1 | 12/2016 | Subotic |
| 2017/0332474 | A1* | 11/2017 | Abs ........................... H01F 3/10 |
| 2017/0332475 | A1* | 11/2017 | Kleeven ................ H05H 7/001 |
| 2018/0116044 | A1 | 4/2018 | Radovinsky |
| 2018/0161598 | A1 | 6/2018 | Antaya |
| 2020/0404772 | A1* | 12/2020 | Antaya ................ H05H 13/005 |

OTHER PUBLICATIONS

Ewa Oponowicz. Gantry Design Using Superconducting Magnet. OMA Topical Workshop on Medical Accelerator Design and Diagnostics. The University of Manchester/The Cockcroft Institute, 22 pp. GSI, Germany Dec. 11-12, 2018.

Arno Godeke. Superconductors in Large Scale Applications: Materials, Production and Purposes. Applied Superconductivity Center, University of Wisconsin-Madison. 22 pp. Retrieved Jun. 30, 2020.

Ainslie et al. Numerical Modelling of Bulk Superconductor Magnetisation. IOP Publishing, Bristol, UK. $^a$ IOP Publishing Ltd 2020. US Office: IOP Publishing, Inc., 190 North Independence Mall West, Suite 601, Philadelphia, PA 19106, USA. 12 pp.Retrieved Jun. 30, 2020.

Ainslie et al. Numerical Modelling of Bulk Superconductor Magnetisation. Chapter 1 Fundamentals of Bulk Superconducting Materials. IOP Science. iopscience.iop.org. 21 pp. Retrieved Jun. 30, 2020.

Yves Jongen. An Introduction to Cyclotrons. PTCoG 47 Education session Jacksonville May 19, 2008. 50 pp.

Timothy A. Antaya. Cyclotron Basics. Unit 10—Lectures 14. MIT Plasma Science and Fusion Center. MIT 8.277/6.808 Intro to Particle Accelerators. 50 pp. Retrieved Jun. 30, 2020.

Timothy A. Antaya. Advanced Cyclotron and Synchrocyclotron Designs. MIT 8.277/6.808 Intro to Particle Accelerators. 38 pp. Retrieved Jun. 30, 2020.

Kleeven et al. Cyclotrons: Magnetic Design and Beam Dynamics. arXiv:1804.08961v1 [physics.med-ph] Apr. 24, 2018. 62 pp.

Paul Heikkinen. Cyclotrons. University of Jyvaskyla, Accelerator Laboratory, Jyvaskyla, Finland. 14 pp.

M.K. Craddock. AG Focusing in the Thomas Cyclotron of 1938. University of British Columbia and TRIUMF. Proceedings of PAC09, Vancouver, BC, Canada FR5REP113. 3 pp.

Hezel et al. The Influence of a Superconducting Split-pair Solenoid as an Insertion Device on the Performance of a Storage Ring for Synchrotron Radiation. Projekt Mikrosystemtechnik. Forschungszentrum Karlsruhe Technik und Umwelt Wissenschaftliche Berichte FZKA 5839. Oct. 1996. 50 pp.

Takahashi et al. A New Concept of a Hybrid Trapped Field Magnet Lens. Superconductor Science and Technology. IOP Publishing Supercond. Sci. Technol. 31 (2018) 044005 (9pp), Published Mar. 7, 2018.

Ainslie et al. Numerical Modelling of Bulk Superconductor Magnetisation. Chapter 1 Fundamentals of Bulk Superconducting Materials. doi:10.1088/978-0-7503-1332-2ch1 $^a$ IOP Publishing Ltd 2020. 22pp.

Takayama et al. Manufacturing of LTS and HTS Magnets for Heavy-Ion Rotating Gantry. Template version 8.0, Jul. 27, 2017. IEEE will put copyright information in this area. See http://www.ieee.org/publications_standards/publications/rights/indes.html for more information. 6pp.

Durrell et al. Bulk Superconductors: A Roadmap to Applications. IOP Publishing. Supercond. Sci. Technol. 31 (2018) 103501 (17pp) Superconductor Science and Technology.

Wikipedia. https://en.wikipedia.org/wiki/Meissner_effect 5pp. Retrieved on Jun. 30, 2020.

Unknown Author. Applied Cyclotrons: Beam Dynamics and Magnetic Design. Retrieved on Jun. 30, 2020.

Wikipedia. Solenoid. Retrieved from "https://en.wikipedia.org/w/index.php?title=Solenoid&oldid=939712031" on Jun. 30, 2020.

Wikipedia. Superconductivity. Retrieved from "https://en.wikipedia.org/w/index.php?title=Solenoid&oldid=939760332" on Jun. 30, 2020.

Unknown Author. modtech@theory.uwinnipeg.ca. Superconductors. Dated Sep. 29, 1999.

Jacob Kelly et al.: "Compact Rare-Earth Superconducting Cyclotron", arxiv.org, Cornell University Library, 201 Olin Library Cornell University Ithaca, NY 14853, Jun. 18, 2019 (Jun. 18, 2019), XP081383136, Figure 3-11, p. 4, right-hand columm, paragraph 3—p. 10, left-hand column, paragraph 2.

\* cited by examiner

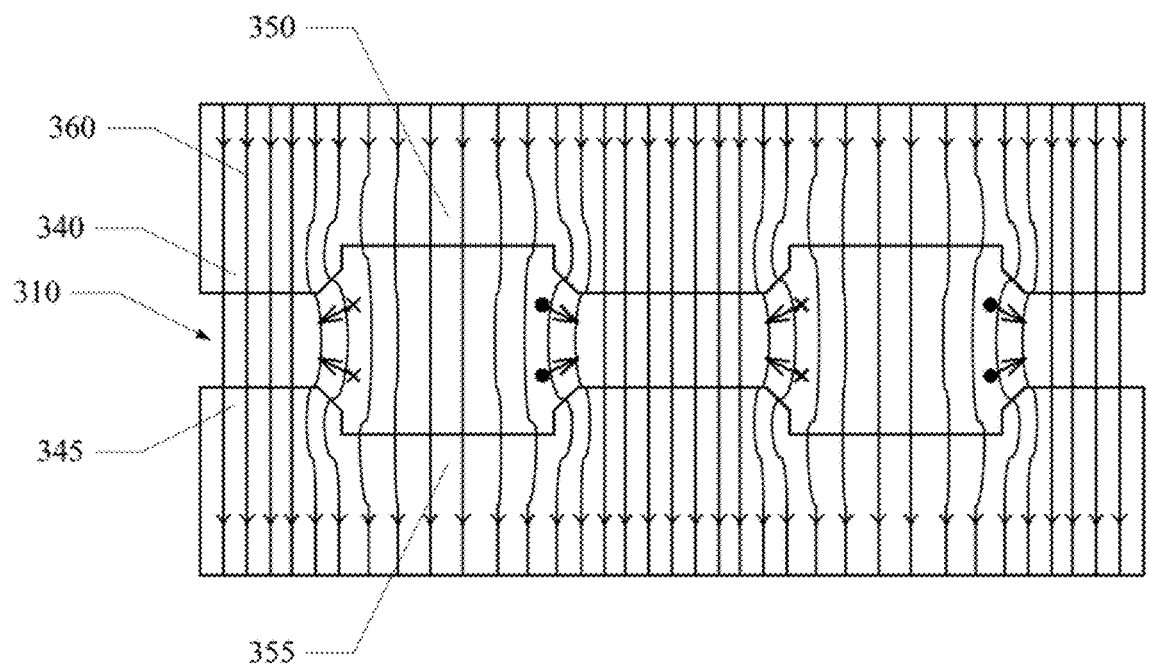
FIG. 3
(Conventional Art)
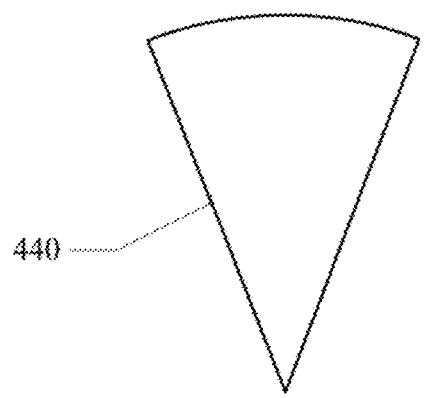 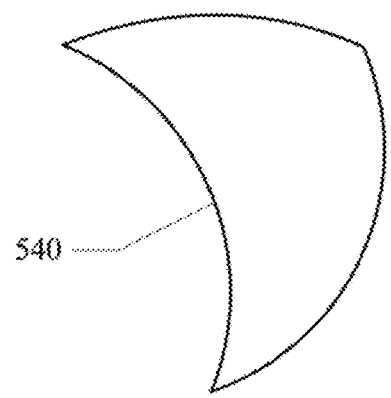
FIG. 4
(Conventional Art)
FIG. 5
(Conventional Art)

1010 — Providing a plurality of pairs of bulk superconductor sectors, wherein each pair of bulk superconductor sectors can be disposed on opposite sides of a median acceleration plane of a beam chamber, and wherein pairs of the bulk superconductor sectors can be separated from each other along a radial arch of the beam chamber

1020 — Providing a magnetic field in the beam chamber having a magnetic flux density that increases radially from the central axis of the beam chamber and is orientated substantially perpendicular to the median acceleration plane, wherein the plurality of pairs of bulk superconductor sectors can be configured to guide or concentrate the magnetic field between the plurality of pairs of bulk superconductor sectors

1030 — Providing charge particles proximate a central axis of the beam chamber

1040 — Providing a radio frequency signal configured to accelerate the charged particles in the beam chamber in an orbital trajectory expanding outward from the central axis of the beam chamber

FIG. 10

1110
Providing a plurality of pairs of structural sectors and a plurality of pairs of bulk superconductor sectors, wherein each pair of magnetically neutral sectors can be disposed on opposite sides of a median acceleration plane of a beam chamber, wherein each pair of bulk superconductor sectors can be disposed on opposite sides of the median acceleration plane, and wherein pairs of the bulk superconductor sectors can be disposed between adjacent pairs of magnetically neutral sectors

1120
Providing a magnetic field in the beam chamber having a magnetic flux density that increases radially from the central axis of the beam chamber and is orientated substantially perpendicular to the median acceleration plane, wherein the plurality of pairs of bulk superconductor sectors can be configured to guide or concentrate the magnetic field from the plurality of pairs of bulk superconductor sectors into the plurality of pairs of structural sectors

1130
Providing charge particles proximate a central axis of the beam chamber

1140
Providing a radio frequency signal configured to accelerate the charged particles in the beam chamber in an orbital trajectory expanding outward from the central axis of the beam chamber

FIG. 11

ISOCHRONOUS CYCLOTRONS EMPLOYING MAGNETIC FIELD CONCENTRATING OR GUIDING SECTORS

BACKGROUND OF THE INVENTION

Referring to FIG. 1, an isochronous cyclotron according to the conventional art is shown. The isochronous cyclotron 100 includes a beam chamber 105 having a central axis and a median acceleration plane. The isochronous cyclotron 100 further includes a particle source 115 configured to introduce charged particles into the beam chamber 105 proximate the central axis of the beam chamber 105.

One or more coils 125 are disposed about the beam chamber 105. The one or more coils 125 are configured to generate a magnetic field in the beam chamber 105 having a magnetic flux density that increases radially from the central axis of the beam chamber 105 and is orientated perpendicularly to the median acceleration plane. One or more radio frequency (RF) drives circuits (not shown) are configured to accelerate the charged particles 220 in the beam chamber 105 in an orbiting trajectory 230 expanding outward from the central axis, as illustrated in FIG. 2. After acceleration along the orbital trajectory 230 the charged particles 220 can be output from the isochronous cyclotron 100, 200 through one or more ports 235.

In the isochronous cyclotron 100, 200 the magnetic field increases with the radius of the beam chamber 105 to keep the angular frequency of the particle constant. As the radius increases, the particle frequency does not depend on the energy of the particle. However, this leads to axial (e.g., vertical) instability in axially symmetric magnetic fields. The axial instability in the magnetic field causes a vertical defocusing wobble in the particle beam.

To compensate for the axial instability, the magnetic field is modified azimuthally to focus the particle beam. To modify the magnetic field azimuthally, the isochronous cyclotron 100, 200, 300 includes a plurality of pairs of sector hills 140, 240, 340, 345 and a plurality of pairs of sector valleys 150, 250, 350, 355 disposed on opposites sides of the median acceleration plane 310, as illustrated in FIG. 3. The sector hills 140, 240, 340, 345 and the sector valleys 150, 250, 350, 355 can be comprised of iron or other ferromagnetic material. FIG. 3 shows a section view along a radial arc of the beam chamber 105. The magnetic field 360 generated by the one or more coils 125 perpendicular to the median acceleration plane 310 is also illustrated. The magnetic flux density is greater between the pairs of sector hills 140, 240, 340, 345 because the sector hills 140, 240, 340, 345 are closer together, while the magnetic flux density is less between the pairs of sector valleys 150, 250, 350, 355. The resulting local densification and de-densification of the magnetic flux density can provide an axial focusing component along the particle path. In addition, the charged particles can experience an axially restoring force at the edges of the sectors. The axially restoring force acts toward the median acceleration plane 310. The dots indicate that the particle has a velocity component into the page and the crosses indicate that the particle has a velocity component toward the page. The incongruity of the magnetic field proximate the boundary between the sector hills 140, 240, 340, 345 and sector valleys 150, 250, 350, 355 providing the axially restoring force is commonly referred to as the flutter field. In some cases, the sector valleys 150, 250, 350, 355 may also be referred to as flutter sectors, flutter plates or the like.

Referring now to FIG. 4, the sector hills and valleys 440 can have a wedge form factor. Alternatively, the sector hills and valleys 540 can have a spiral form factor, as shown in FIG. 5. The spiral shape of the sector hills and valleys 540 can provide additional axial focusing.

A larger average magnetic field 360 that provides a tighter spiral deflection of the charged particles 220 enables the size of the isochronous cyclotron 100, 200 to be reduced. However, as the average magnetic field 360 is increased, the flutter field decreases relative to the average magnetic field. Therefore, the axial instability increases. Furthermore, the ferromagnetic sectors saturate when the magnetic field is increased beyond the magnetic saturation limit of the sector material. When the ferromagnetic sectors saturate, the sectors cannot generate the flutter fields at their boundaries that are used to provide axial focusing.

To provide additional magnetic flutter field flux, the valley sectors 640 can further include an electromagnetic coil 645 disposed about the perimeter of the valley sectors 640, as illustrated in FIG. 6. In one implementation, the electromagnetic coil 645 disposed about the perimeter of the valley sectors 640 can be a superconductor coil. However, the superconductor coil increases the complexity as a result of the need for routing current to and from the valley sectors, the need for cooling the valley sectors below the critical temperature of the superconductor of the coils, and the like. In addition, isochronous cyclotrons typically include twelve to twenty valley sectors 640. Therefore, the amount of superconductor coil 645 used for wrapping the valley sectors 640 can result in an appreciable cost increase in the isochronous cyclotron 100, 200. In addition, the preferable sharp tips of the valley sectors 640 need to be rounded to accommodate the coil 645 disposed about the perimeter of the valley sectors 640. Furthermore, the concave sections of the preferred spiral shape of the valley sectors 640 increase the complexity of winding the coil 645 about the perimeter of the valley sectors.

Accordingly, there is a continuing need for improved particle acceleration techniques in isochronous cyclotrons to permit further reductions in the size and or cost of the isochronous cyclotrons.

SUMMARY OF THE INVENTION

The present technology may best be understood by referring to the following description and accompanying drawings that are used to illustrate embodiments of the present technology directed toward generation of flutter fields in isochronous cyclotrons.

In one embodiment, an isochronous cyclotron can include a beam chamber, a particle source, a plurality of pairs of bulk superconductor sectors, one or more coils, and one or more radio frequency drive circuits. The beam chamber can include a central axis and a median acceleration plane. The particle source can be coupled to the median acceleration plane proximate the central axis of the beam chamber. The one or more coils can be disposed about the beam chamber. The one or more radio frequency drive circuits can be configured to accelerate charged particles in an orbital trajectory expanding outward from the central axis. Each pair of bulk superconductor sectors can be disposed on opposite side of the median acceleration plane.

In another embodiment, a charged particle acceleration method can include providing a beam chamber and a plurality of pairs of bulk superconductor sectors. Each pair of bulk superconductor sectors can also be disposed on opposite sides of a median acceleration plane of the beam chamber. In addition, pairs of the bulk superconductor sectors can be spaced apart from each other along a radial arch of the beam chamber. The method further includes providing a magnetic field in the beam chamber having a magnetic flux density that increases radially from the central axis of the beam chamber and is orientated substantially perpendicular to the median acceleration plane. In addition, the plurality of pairs of bulk superconductor sectors can be configured to guide or concentrate at least a portion of the magnetic field between the plurality of pairs of bulk superconductor sectors.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Embodiments of the present technology are illustrated byway of example and not by way of limitation, in the figures of the accompanying drawings and in which like reference numerals refer to similar elements and in which:

FIG. 3 shows a section view along a radial arc of the beam chamber according to the conventional art.

FIG. 4 shows a form factor of sectors of a beam chamber according to the conventional art.

FIG. 5 shows another form factor of sectors of a beam chamber according to the conventional art.

FIG. 10 shows a charged particle acceleration method, in accordance with aspects of the present technology.

FIG. 11 shows a charged particle acceleration method, in accordance with aspects of the present technology.

DETAILED DESCRIPTION OF THE INVENTION

Figure 1:
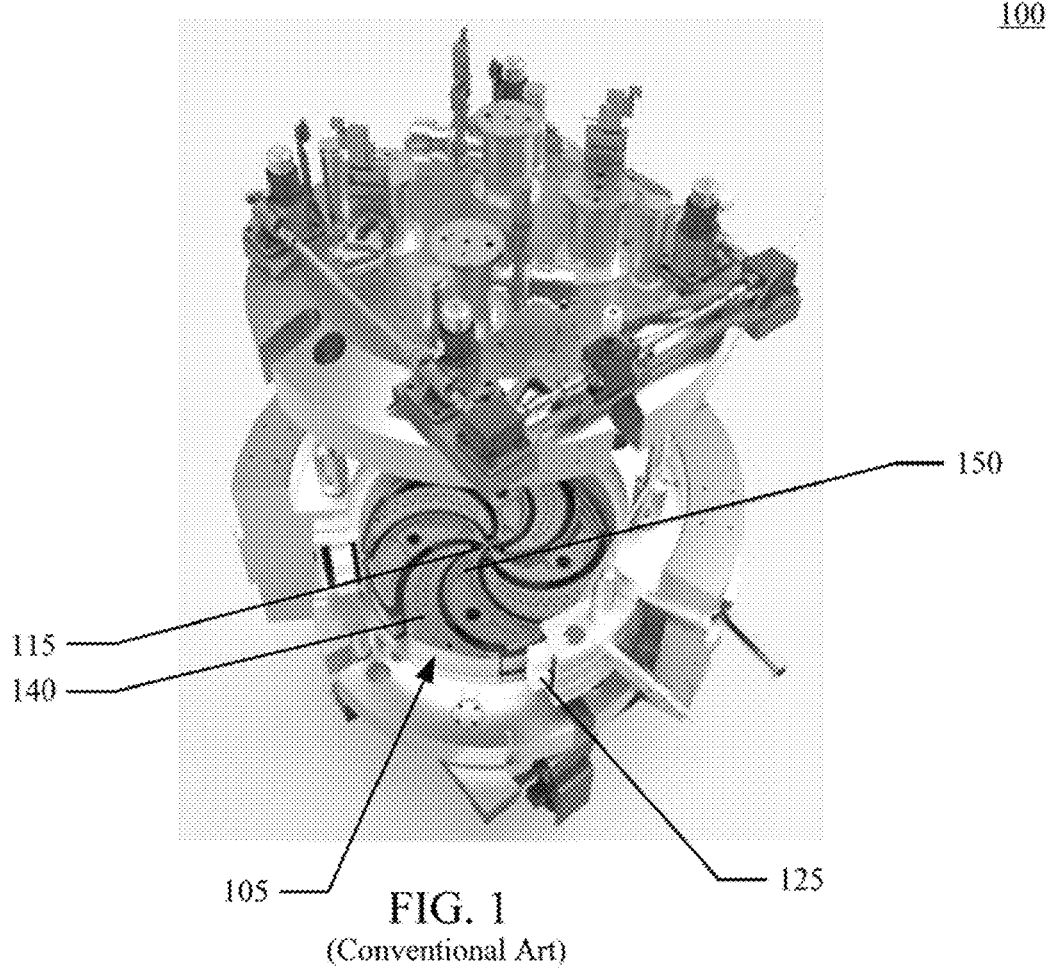
FIG. 1 shows an isochronous cyclotron according to the conventional art.
Figure 2:
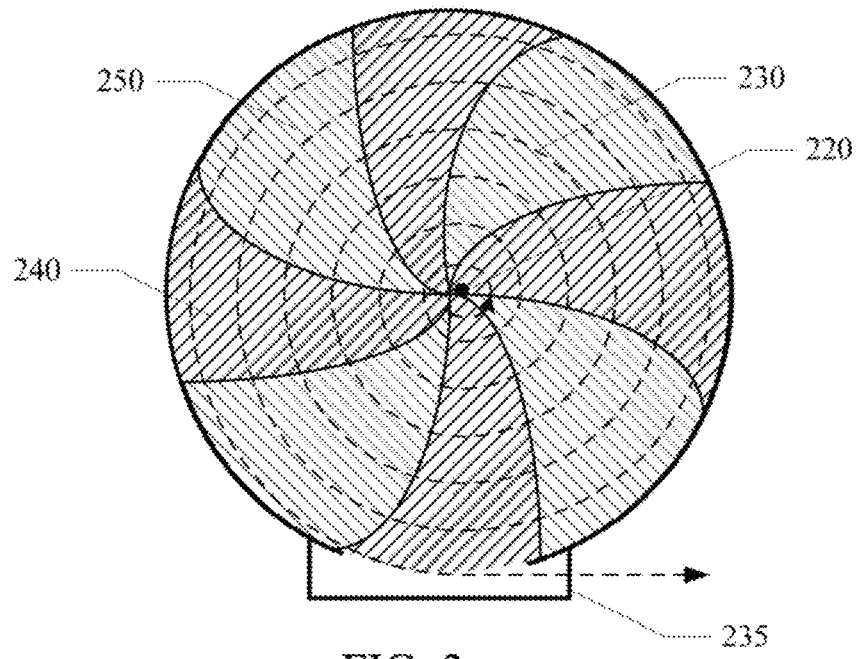
FIG. 2 shows a beam chamber of an isochronous cyclotron according to the conventional art.
Figure 6:
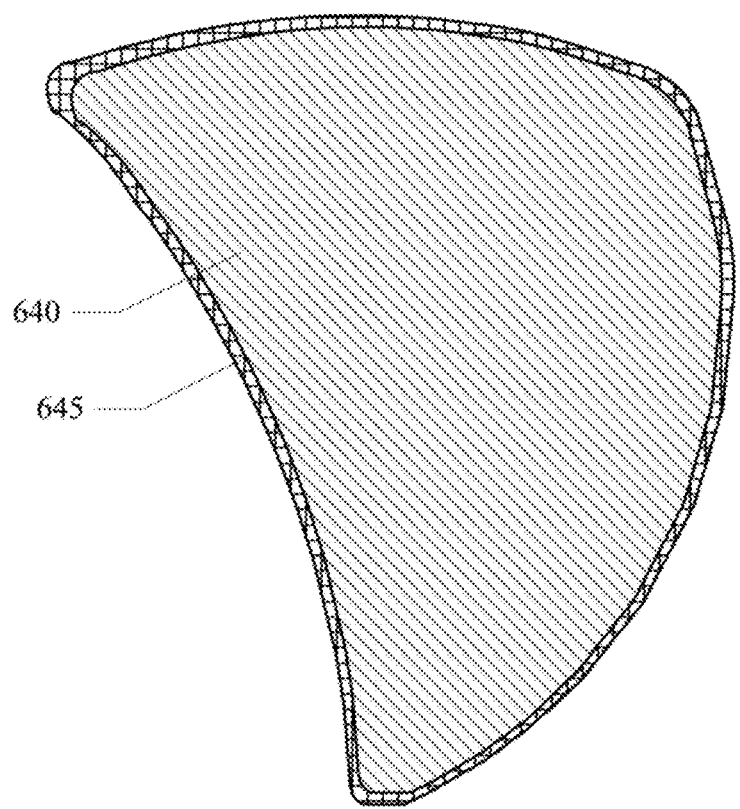
FIG. 6 shows an electromagnetic coil wrapped valley sector according to the conventional art.

Reference will now be made in detail to the embodiments of the present technology, examples of which are illustrated in the accompanying drawings. While the present technology will be described in conjunction with these embodiments, it will be understood that they are not intended to limit the technology to these embodiments. On the contrary, the invention is intended to cover alternatives, modifications and equivalents, which may be included within the scope of the invention as defined by the appended claims. Furthermore, in the following detailed description of the present technology, numerous specific details are set forth in order to provide a thorough understanding of the present technology. However, it is understood that the present technology may be practiced without these specific details. In other instances, well-known methods, procedures, components, and circuits have not been described in detail as not to unnecessarily obscure aspects of the present technology.

Some embodiments of the present technology which follow are presented in terms of routines, modules, logic blocks, and other symbolic representations of operations on data within one or more electronic devices. The descriptions and representations are the means used by those skilled in the art to most effectively convey the substance of their work to others skilled in the art. A routine, module, logic block and/or the like, is herein, and generally, conceived to be a self-consistent sequence of processes or instructions leading to a desired result. The processes are those including physical manipulations of physical quantities. Usually, though not necessarily, these physical manipulations take the form of electric or magnetic signals capable of being stored, transferred, compared and otherwise manipulated in an electronic device. For reasons of convenience, and with reference to common usage, these signals are referred to as data, bits, values, elements, symbols, characters, terms, numbers, strings, and/or the like with reference to embodiments of the present technology.

It should be borne in mind, however, that these terms are to be interpreted as referencing physical manipulations and quantities and are merely convenient labels and are to be interpreted further in view of terms commonly used in the art. Unless specifically stated otherwise as apparent from the following discussion, it is understood that through discussions of the present technology, discussions utilizing the terms such as "receiving," and/or the like, refer to the actions and processes of an electronic device such as an electronic computing device that manipulates and transforms data. The data is represented as physical (e.g., electronic) quantities within the electronic device's logic circuits, registers, memories and/or the like, and is transformed into other data similarly represented as physical quantities within the electronic device.

In this application, the use of the disjunctive is intended to include the conjunctive. The use of definite or indefinite articles is not intended to indicate cardinality. In particular, a reference to "the" object or "a" object is intended to denote also one of a possible plurality of such objects. The use of the terms "comprises," "comprising," "includes," "including" and the like specify the presence of stated elements, but do not preclude the presence or addition of one or more other elements and or groups thereof. It is also to be understood that although the terms first, second, etc. may be used herein to describe various elements, such elements should not be limited by these terms. These terms are used herein to distinguish one element from another. For example, a first element could be termed a second element, and similarly a second element could be termed a first element, without departing from the scope of embodiments. It is also to be understood that when an element is referred to as being "coupled" to another element, it may be directly or indirectly connected to the other element, or an intervening element may be present. In contrast, when an element is referred to as being "directly connected" to another element, there are not intervening elements present. It is also to be understood that the term "and or" includes any and all combinations of one or more of the associated elements. It is also to be understood that the phraseology and terminology used herein is for the purpose of description and should not be regarded as limiting.

Isochronous cyclotrons can generate a continuous high current particle beam that can be utilized in for example, but not limited to, proton therapy systems for fast patient throughput and modern treatment modalities of cancer, tumors and the like. Aspects of the present technology provide isochronous cyclotrons employing magnetic field concentrating or guiding sectors. The magnetic field concentrating or guiding sectors can be passive bulk superconductor sectors. The bulk superconductor sectors can be configured to generate beam focusing oscillating magnetic fields, commonly referred to as flutter fields, along the beam trajectory in the isochronous cyclotron. The oscillating magnetic field, finetuned by the guiding and or concentrating bulk superconductor sectors, work as magnetic lenses to shape and or guide a main field of a particle beam. The oscillating magnetic field generated by the guiding and or concentrating bulk superconductor sectors can allow the use of higher magnetic fields in the beam chamber without a practical magnetic field limitation. Therefore, the size and cost of isochronous cyclotrons can be reduced.

Figure 7A:
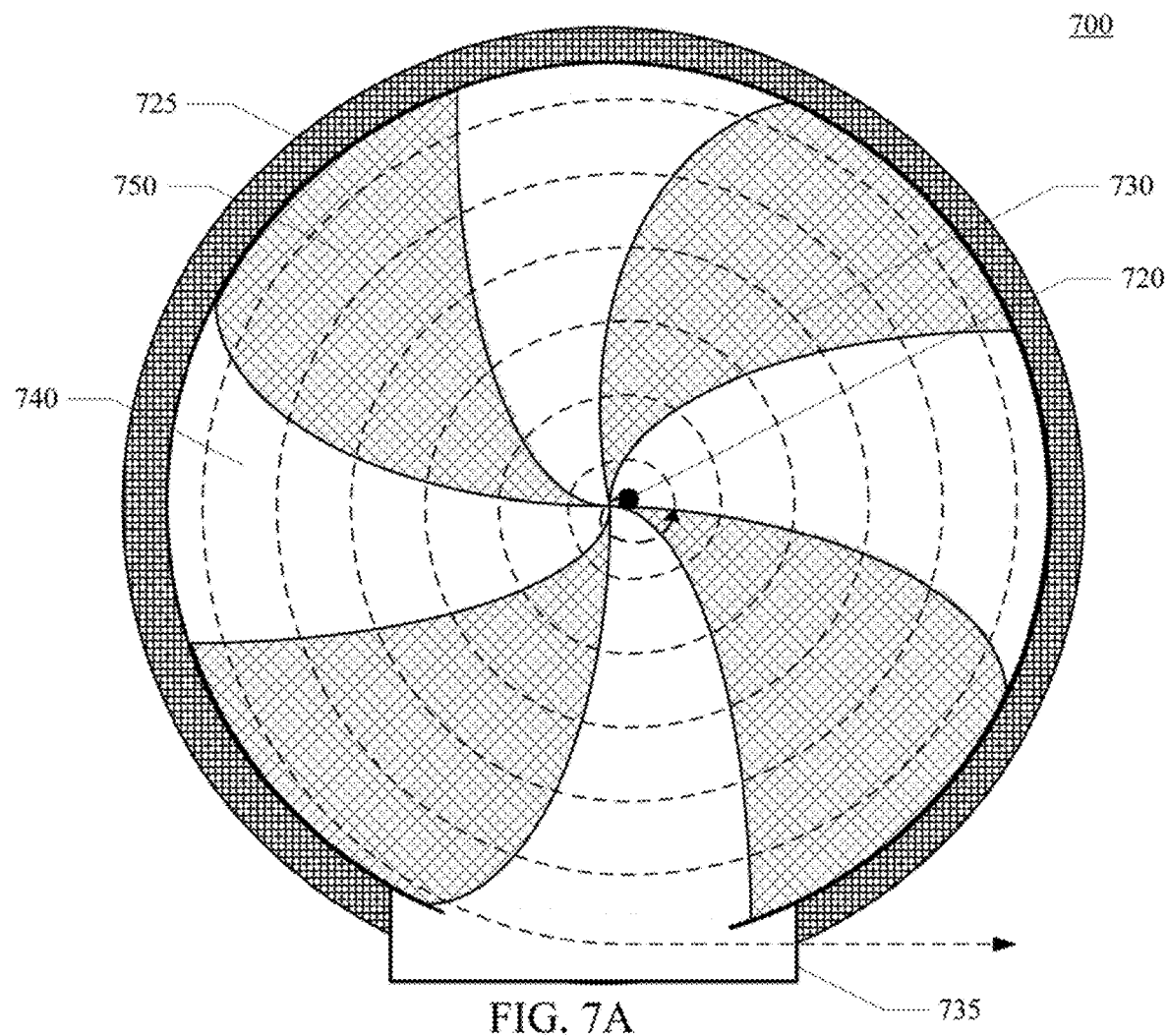
FIGS. 7A and 7B show an isochronous cyclotron, in accordance with aspects of the present technology.
Figure 7B:
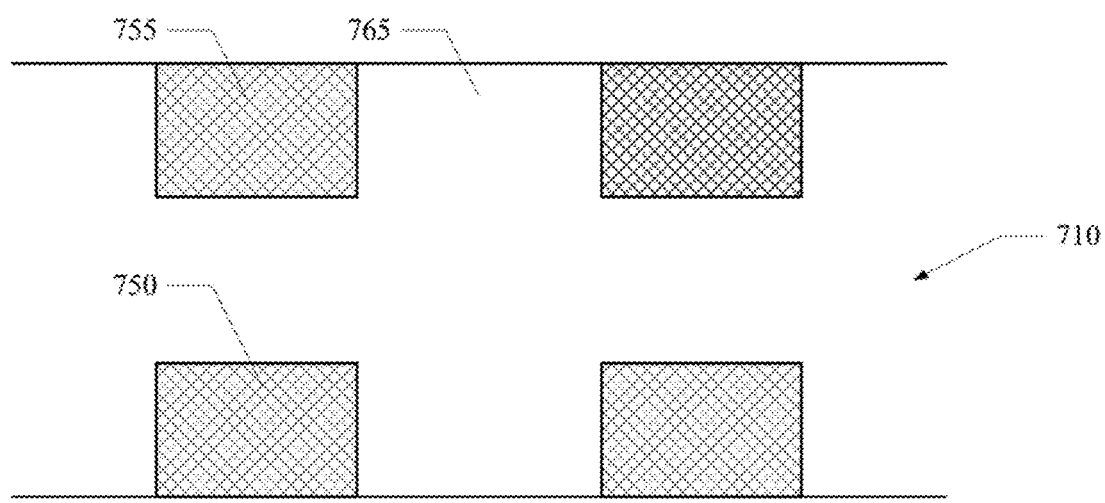

Referring now to FIGS. 7A and 7B, a beam chamber of an isochronous cyclotron, in accordance with aspects of the present technology, is shown. FIG. 7A illustrates a planar view of one side of the beam chamber. FIG. 7B illustrates a section view along a radial arc of the beam chamber. The isochronous cyclotron 700 can include a beam chamber having a central axis and a median acceleration plane 710. The isochronous cyclotron 700 can further include a particle source configured to introduce charged particles 720 into the beam chamber proximate the central axis of the beam chamber. In one implementation, the particle source can be located proximate the central axis of the beam chamber. In another implementation, the particle source can inject particles into the beam chamber proximate the central axis of the beam chamber. As used herein, the beam chamber refers to the region in which the charged particles are accelerated. In one implementation, the beam chamber can be a region within a vacuum chamber (not shown).

One or more coils 725 can be disposed about the beam chamber. The one or more coils 725 can be configured to generate a magnetic field in the beam chamber having a magnetic flux density that increases radially from the central axis of the beam chamber and is orientated substantially perpendicularly to the median acceleration plane 710. In one implementation, the one or more coils 725 can include a pair of magnetic coils encircling the central axis and disposed on opposite sides of the median acceleration plane 710 of the beam chamber. Current passing through the one or more coils 725 generates a magnetic field perpendicular to the median acceleration plane 710 with radial increasing flux density. In one implementation, the one or more coils 725 can be one or more superconductor coils. In one implementation, the superconductor of the one or more coils 725 can be a high-temperature superconductor. In another implementation, the superconductor of the one or more electromagnetic coils 725 can be a medium-temperature superconductor.

The isochronous cyclotron 700 can further include a plurality of pairs of bulk superconductor sectors 750, 755. The plurality of pairs of bulk superconductor sectors 750, 755 can be disposed inside or outside the beam chamber and or vacuum chamber. The plurality of pairs of bulk superconductor sectors 750, 755 can be disposed on opposites sides of the median acceleration plane 710, wherein pairs of the bulk superconductor sectors 750, 755 are spaced apart 765 from each other along a radial arch of the beam chamber. In one implementation, the plurality of pairs of bulk superconductor sectors 750, 755 can include a bulk high-temperature superconductor. In another implementation, the bulk superconductor sectors 750, 755 can include a bulk medium-temperature superconductor. The bulk high-temperature superconductor material can include, but is not limited to, rare-earth barium copper oxides (REBCO) such as yttrium barium copper oxide (YBCO), or gadolinium barium copper oxide (GdBCO), or europium barium copper oxide (EUBCO), lanthanum barium copper oxide (LBCO), and different types of bismuth strontium calcium copper oxide (BSCCO). The bulk medium-temperature superconductor material can include, but is not limited to, magnesium diboride (MgB2), or iron (Fe) based superconductors, also referred to as Pnictides. As used herein the term bulk superconductor material refers to superconductor materials, as opposed to structures that comprise a combination of superconductor material in combination with a resistive conductor such as copper, silver or the like which are also commonly referred to as superconductors and which typically are manufactured in the form of elongated strips, tapes or wires. As used herein high-temperature superconductor material refers to materials that exhibit superconductivity above about 40 Kelvin (K). As used herein medium-temperature superconductor material refers to materials that exhibit superconductivity above about 25 Kelvin (K). In one implementation, the plurality of pairs of bulk superconductor sectors 750, 755 can include a bulk type-II superconductor. In one implementation, the bulk type-II superconductor can be maintained in a mixed state by one or more coolers (not shown) thermally coupled to the plurality of pairs of bulk superconductor sectors 750, 755. The one or more coolers can include one or more electric cryocoolers, cryogen-baths or the like.

Although FIG. 7A illustrates four pairs of bulk superconductor sectors 750, 755, the isochronous cyclotron 700 can include any number of pairs of bulk superconductor sectors 750, 755. In addition, the guiding and or concentrating of the magnetic field by the bulk superconductor sectors 750, 755, and in turn the axial focusing by the magnetic flux, can be a combination of the bulk superconductor sector dimensions, shape and density, as well as other physical properties. For example, in one implementation, the plurality of pairs of bulk superconductor sectors 750, 755 can have a wedge shape form factor. In another implementation, the plurality of pairs of bulk superconductor sectors 750, 755 can have a spiral shape form factor. In one implementation, the plurality of pairs of bulk superconductor sectors 750, 755 can have beveled edges. In one implementation, plurality of pairs of bulk superconductor sectors 750, 755 can have raised edges. In one implementation, the plurality of pairs of bulk superconductor sectors 750, 755 can have radial width substantially equal to the radial spacing between adjacent bulk superconductor sectors 750, 755. In another implementation, the plurality of pairs of bulk superconductor sectors 750, 755 can have radial widths substantially wider than the radial spacing between adjacent bulk superconductor sector 750, 755. In yet another implementation, the plurality of pairs of bulk superconductor sectors 750, 755 can have radial widths substantially narrower than the radial spacing between adjacent bulk super conductor sectors 750, 755. In one implementation, the gaps 765 between the plurality of pairs of bulk superconductor sectors 750, 755 can be filled with a mechanical reinforcement (not shown), such as a metal or ceramic reinforcement, glass fiber reinforced epoxy resin, a carbon fiber reinforced polymer, or similar.

A radio frequency drive circuit (not shown) can be configured to accelerate the charged particles 720 in the beam chamber in an orbiting trajectory 730 expanding outward from the central axis. In one implementation, the radio frequency (RF) drives can be disposed radially between adjacent pairs of the bulk superconductor sectors 750, 755 (not shown) to accelerate the particles. After acceleration along the orbital trajectory 730, the charged particles 720 can be output from the isochronous cyclotron 700 through one or more ports 735.

Figure 8A:
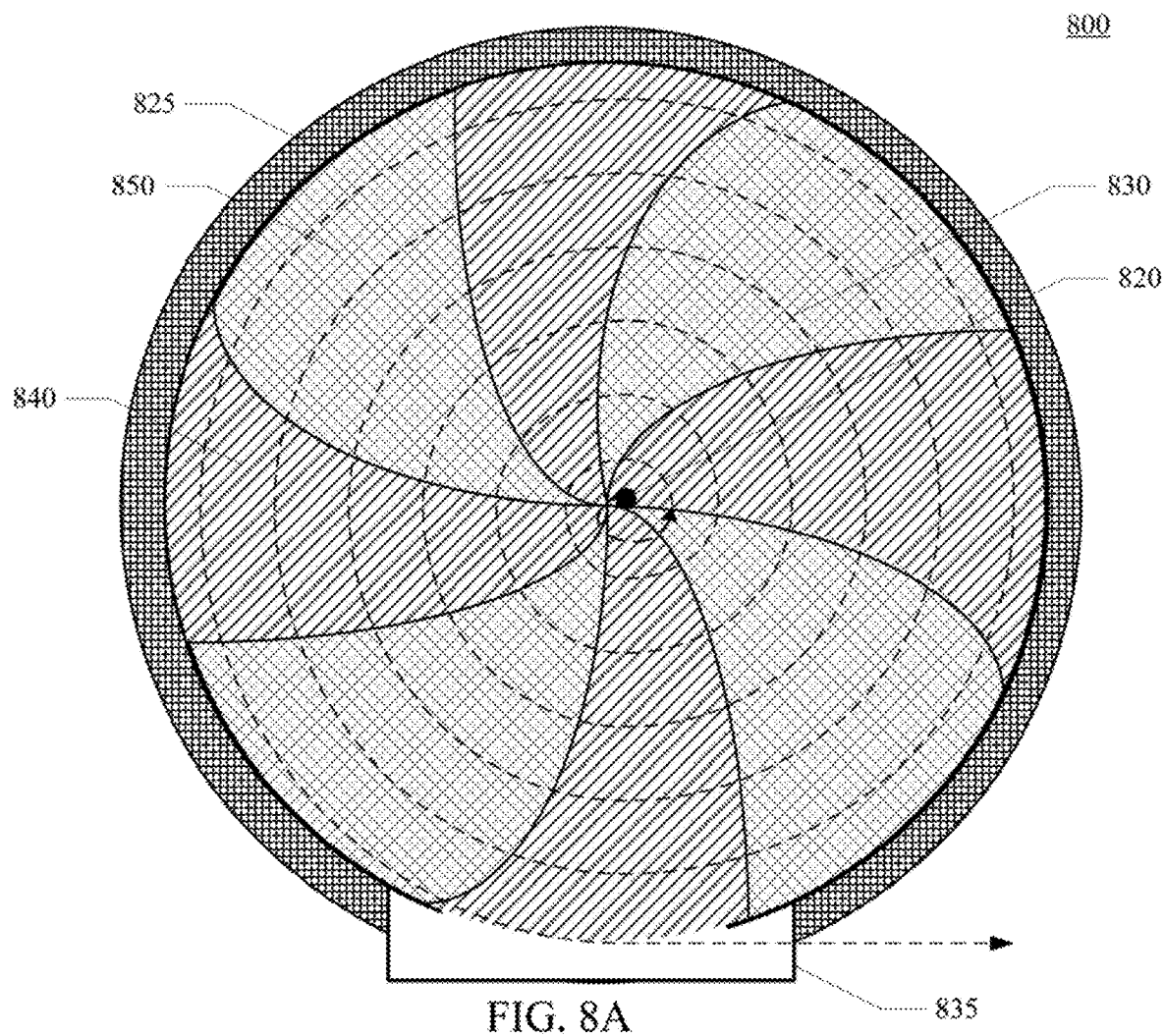
FIGS. 8A and 8B show an isochronous cyclotron, in accordance with aspects of the present technology.
Figure 8B:
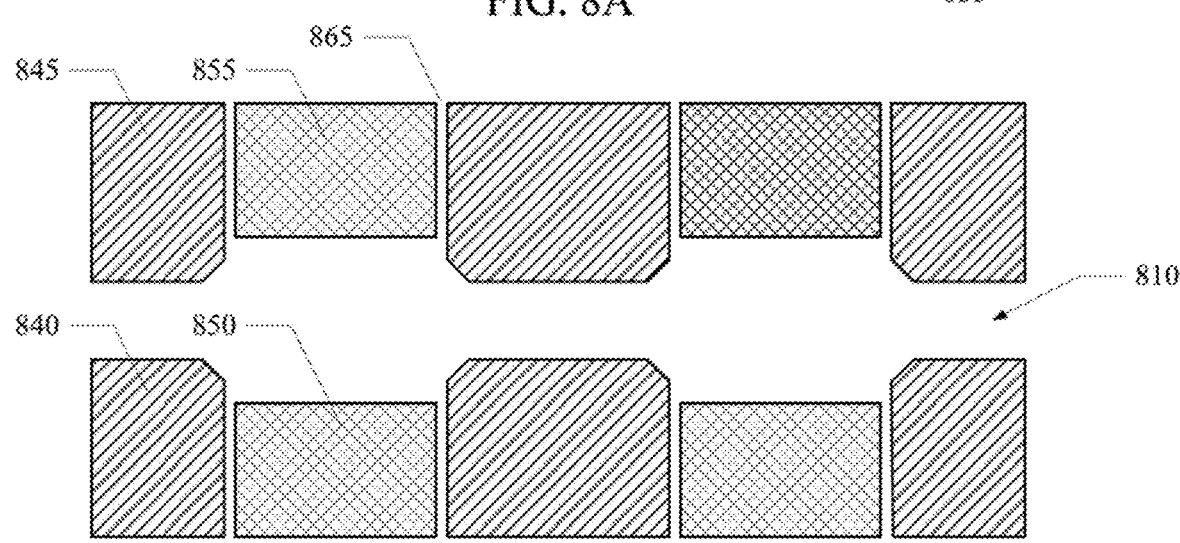

Referring now to FIGS. 8A and 8B, a beam chamber of an isochronous cyclotron, in accordance with aspects of the present technology, is shown. FIG. 8A illustrates a planar view of one side of the beam chamber. FIG. 8B illustrates a section view along a radial are of the beam chamber. The isochronous cyclotron 800 can include a beam chamber having a central axis and a median acceleration plane 810. The isochronous cyclotron 800 can further include a particle source configured to introduce charged particles 820 into the beam chamber proximate the central axis of the beam chamber. In one implementation, the particle source can be located proximate the central axis of the beam chamber. In another implementation, the particle source can inject particles into the beam chamber proximate the central axis of the beam chamber.

One or more coils 825 can be disposed about the beam chamber. The one or more coils 825 can be configured to generate a magnetic field in the beam chamber having a magnetic flux density that increases radially from the central axis of the beam chamber and is orientated substantially perpendicularly to the median acceleration plane 810. In one implementation, the one or more coils 825 can include a pair of coils encircling the central axis and disposed on opposite sides of the median acceleration plane 810 of the beam chamber. Current passing through the one or more coils 825 generates a magnetic field perpendicular to the median acceleration plane 810 with radial increasing flux density. In one implementation, the one or more coils 825 can be one or more superconductor coils. In one implementation, the superconductor of the one or more coils 825 can be a high-temperature superconductor. In another implementation, the superconductor of the one or more coils 825 can be a medium-temperature superconductor.

The isochronous cyclotron 800 can further include a plurality of pairs of structural sectors 840, 845 and a plurality of pairs of bulk superconductor sectors 850, 855. The plurality of pairs of structural sectors 840, 845 and the plurality of pairs of bulk superconductor sectors 850, 855 can be disposed inside or outside the beam chamber and or vacuum chamber. The plurality of pairs of structural sectors 840, 845 and the plurality of pairs of bulk superconductor sectors 850, 855 can be disposed on opposites sides of the median acceleration plane 810. In one implementation, an axial separation between respective pairs of the bulk superconductor sectors 850, 855 can be greater or smaller than an axial separation between respective pairs of the structural sectors 840, 845. In one implementation, the plurality of pairs of structural sector 840, 845 can be comprised of a magnetically neutral material, such as but not limited to a metal, a ceramic, a glass fiber reinforced epoxy resin, a carbon fiber reinforced polymer, or similar. In another implementation, the plurality of pairs of structural sectors 840, 845 can be comprised of ferromagnetic, paramagnetic and or diamagnetic material, such as but not limited to iron. In one implementation, the plurality of pairs of bulk superconductor sectors 850, 855 can include a bulk high-temperature superconductor material. In another implementation, the bulk superconductor sectors 850, 855 can include a bulk medium-temperature superconductor material. The bulk high-temperature superconductor material can include, but is not limited to, rare-earth barium copper oxides (RE-BCO) such as yttrium barium copper oxide (YBCO), or gadolinium barium copper oxide (GdBCO), or europium barium copper oxide (EUBCO), lanthanum barium copper oxide (LBCO), and different types of bismuth strontium calcium copper oxide (BSCCO). The bulk medium-temperature superconductor material can include, but is not limited to, magnesium diboride (MgB2), or iron (Fe) based superconductors, also referred to as Pnictides As used herein the term bulk superconductor material refers to superconductor materials, as opposed to structures that comprise a combination of superconductor material in combination with a resistive conductor such as copper, silver or the like which are also commonly referred to as superconductors and which typically are manufactured in the form of elongated strips, tapes or wires. As used herein high-temperature superconductor material refers to materials that exhibit superconductivity above about 40 Kelvin (K). As used herein medium-temperature superconductor material refers to materials that exhibit superconductivity above about 25 Kelvin (K). In one implementation, the plurality of pairs of bulk superconductor sectors 850, 855 can include a bulk type-II superconductor. In one implementation, the bulk type-li superconductor can be maintained in a mixed state by one or more coolers (not shown) thermally coupled to the plurality of pairs of bulk superconductor sectors 850, 855. The one or more coolers can include one or more electric cryocoolers, cryogen-baths or the like.

Although FIG. 8A illustrates four pairs of structural sectors 840, 845 and four pairs of bulk superconductor sectors 850, 855, the isochronous cyclotron 800 can include any number of pairs of structural sectors 840, 845 and bulk superconductor sectors 850, 855. In addition, the guiding and or concentrating of the magnetic field by the bulk superconductor sectors 850, 855, and in turn the axial focusing by the magnetic flux, can be a combination of the bulk superconductor material type, sector dimensions, shape and density, as well as other physical properties. For example, in one implementation, the plurality of pairs of structural sectors 840, 845 and the plurality of pairs of bulk superconductor sectors 850, 855 can have a wedge shape form factor. In another implementation, the plurality of pairs of structural sectors 840, 845 and the plurality of pairs of bulk superconductor sectors 850, 855 can have a spiral shape form factor. In one implementation, the plurality of pairs of structural sectors 840, 845 and or the plurality of pairs of bulk superconductor sectors 850, 855 can have beveled edges. In one implementation, the plurality of pairs of structural sectors 840, 845 and or the plurality of pairs of bulk superconductor sectors 850, 855 can have raised edges. In one implementation, the plurality of pairs of structural sectors 840, 845 and the plurality of pairs of bulk superconductor sectors 850, 855 can have substantially equal radial widths. In another implementation, the plurality of pairs of structural sectors 840, 845 can have a substantially wider radial width as compared to plurality of pairs of bulk superconductor sectors 850, 855. In yet another implementation, the plurality of pairs of structural sectors 840, 845 can have a substantially narrower radial width as compared to plurality of pairs of bulk superconductor sectors 850, 855. In one implementation, the plurality of pairs of structural sectors 840, 845 and the plurality of pairs of bulk superconductor sectors 850, 855 can substantially abut each other. In another implementation, gaps 865 can be disposed between the plurality of pairs of structural sectors 840, 845 and the plurality of pairs of bulk superconductor sectors 850, 855. In one implementation, the gaps 865 between the plurality of pairs of structural sectors 840, 845 and the plurality of pairs of bulk superconductor sectors 850, 855 can be filled with a mechanical reinforcement, such as a glass fiber reinforced epoxy resin, a carbon fiber reinforced polymer, or similar.

A radio frequency drive circuit (not shown) can be configured to accelerate the charged particles 820 in the beam chamber in an orbiting trajectory 830 expanding outward from the central axis. After acceleration along the orbital trajectory 830, the charged particles 820 can be output from the isochronous cyclotron 800 through one or more ports 835.

Figure 9:
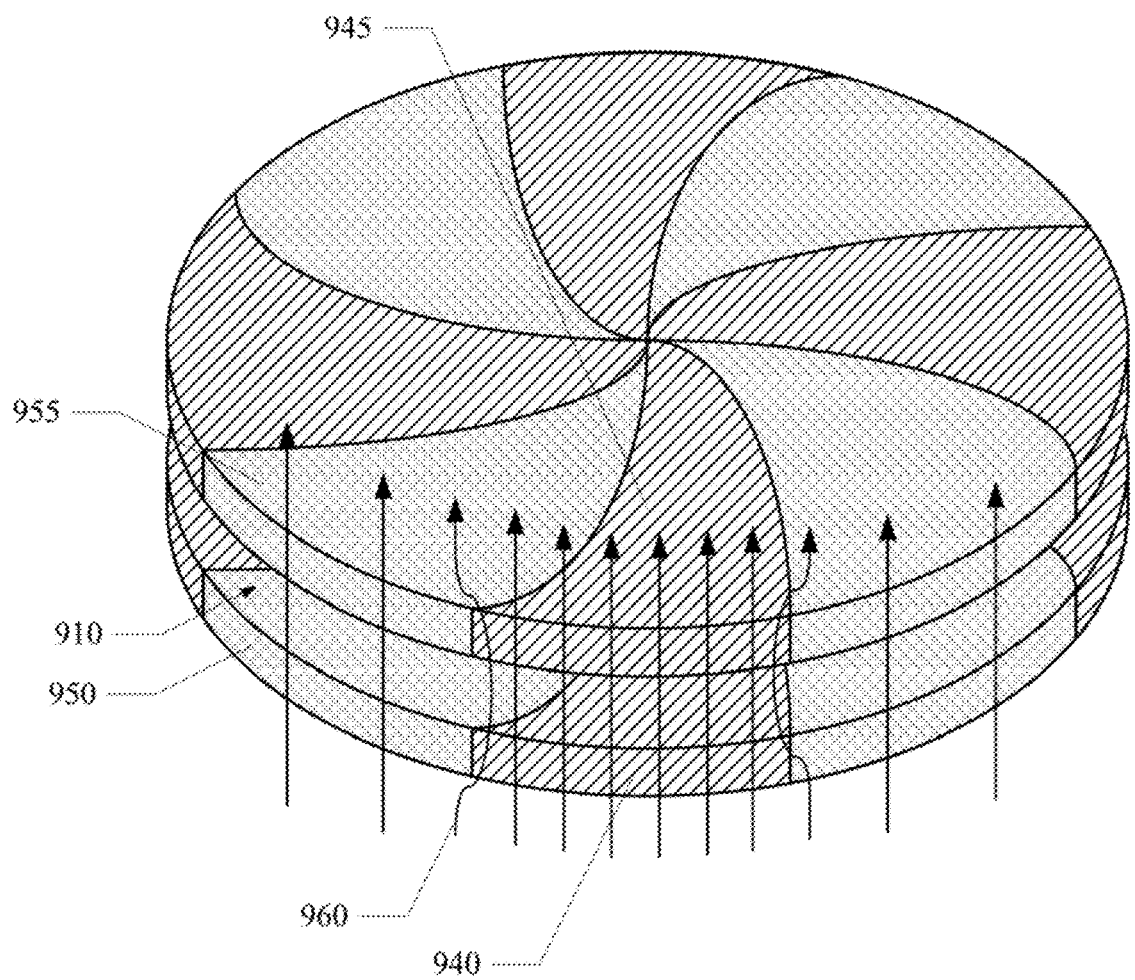
FIG. 9 shows a beam chamber of an isochronous cyclotron, in accordance with aspects of the present technology.

Referring now to FIG. 9, a portion of a beam chamber including a plurality of pairs of structural sectors and a plurality of pairs of bulk superconductor sectors, in accordance with aspects of the present technology is shown. A plurality of pairs of structural sectors 940, 945 can be disposed on opposite sides of a median acceleration plane 910 of the beam chamber. A plurality of pairs bulk superconductor sectors 950, 955 can also be disposed on opposite sides of the median acceleration plane 910. Pairs of the bulk superconductor sectors 950, 955 can be disposed between adjacent pairs of structural sectors 940, 945. The plurality of pairs of bulk superconductor sectors 950, 955 can be configured to guide and or concentrate the magnetic field 960 from the plurality of pairs of bulk superconductor sectors 950, 955 into the plurality of pairs of structural sectors 940, 945. The guiding and or concentrating of the magnetic field 960 causes a local densification and de-densification of the magnetic flux density (e.g., flutter field), thereby provide the axial focusing component along the particle path.

In one implementation, the plurality of pairs of bulk superconductor sectors 950, 955 can include bulk type-II superconductor that is maintained in a mixed state. In the mixed state (e.g., above the lower critical magnetic field $Hc_1$ but below the upper critical magnetic field $Hc_2$), a portion of the magnetic field 960 can penetrate through the bulk type-II superconductor sectors 950, 955 to provide a lower magnetic flux, and the other portion of the magnetic field 960 is guided to and concentrated into the structural sectors 940, 945, as illustrated in FIG. 9. In one implementation, the magnetic field 960 guided to and concentrated in the median acceleration plane 910 proximate the structural sectors 940, 945, by the bulk type-II superconductor sectors 950, 955, provides an axial focusing component of the magnetic field 960.

In one implementation, the plurality of pairs of structural sectors 940, 945 and the plurality of pairs of bulk superconductor sectors 950, 955 can have form factors configured to further increase the axial focusing component of the magnetic field 960. For example, the plurality of pairs of bulk superconductor sectors 850, 855, 950, 955 and the plurality of pairs of structural sectors 840, 845, 940, 945 can have a spiral shape that further provides an axial focusing component to the magnetic field 960.

Referring now to FIG. 10, a charged particle acceleration method, in accordance with aspects of the present technology, is shown. The method can include providing a plurality of pairs of bulk superconductor sectors, at 1010. Each pair of bulk superconductor sectors can be disposed on opposite sides of a median acceleration plane of a beam chamber. In addition, pairs of the bulk superconductor sectors can be separated from each other along a radial arch of the beam chamber.

At 1020, a magnetic field can be provided in the beam chamber. The magnetic field can have a magnetic flux density that increases radially from the central axis of the beam chamber and can be orientated substantially perpendicular to the median acceleration plane. The plurality of pairs of bulk superconductor sectors can be configured to guide and or concentrate the magnetic field between the plurality of pairs of bulk superconductor sectors.

At 1030, charged particles can be provided proximate a central axis of the beam chamber. In one implementation, the charged particles can be protons. In other implementations, the charged particles can be electrons. In yet another implementation, the charged particles can be ions of any type (e.g., C+) or the like. At 1040, a radio frequency signal can be provided to accelerate the charged particles in the beam chamber in an orbital trajectory expanding outward from the central axis of the beam chamber. The magnetic field guiding and or concentrating provided by the plurality of pairs of bulk superconductor sectors can provide a beam focusing oscillation in the provided magnetic field to offset axial instability in the orbital trajectory.

Referring now to FIG. 11, a charged particle acceleration method, in accordance with aspects of the present technology, is shown. The method can include providing a plurality of pairs of structural sectors and a plurality of pairs of bulk superconductor sectors, at 1110. Each pair of structural sectors can be disposed on opposite sides of a median acceleration plane of a beam chamber. Likewise, each pair of bulk superconductor sectors can be disposed on opposite sides of the median acceleration plane. In addition, pairs of the bulk superconductor sectors can be disposed between adjacent pairs of structural sectors. In one implementation, the plurality of pairs of structural sectors can include a magnetically neutral material. In another implementation, the plurality of pairs of structural sectors can include a ferromagnetic, paramagnetic, and or diamagnetic material. In one implementation, the plurality of pairs of bulk superconductor sectors can be configured for nearly full magnetic field exclusion or partial magnetic field exclusion.

At 1120, a magnetic field can be provided in the beam chamber. The magnetic field can have a magnetic flux density that increases radially from the central axis of the beam chamber and can be orientated substantially perpendicular to the median acceleration plane. The plurality of pairs of bulk superconductor sectors can be configured to guide and or concentrate the magnetic field from the plurality of pairs of bulk superconductor sectors into the plurality of pairs of structural sectors.

At 1130, charged particles can be provided proximate a central axis of the beam chamber. In one implementation, the charged particles can be protons. In other implementations, the charged particles can be electrons. In yet another implementation, the charged particles can be ions of any type (e.g., C+) or the like. At 1140, a radio frequency signal can be provided to accelerate the charged particles in the beam chamber in an orbital trajectory expanding outward from the central axis of the beam chamber. The magnetic field guiding and or concentrating provided by the plurality of pairs of bulk superconductor sectors can provide a beam focusing oscillation in the provided magnetic field to offset axial instability in the orbital trajectory.

Figure 12:
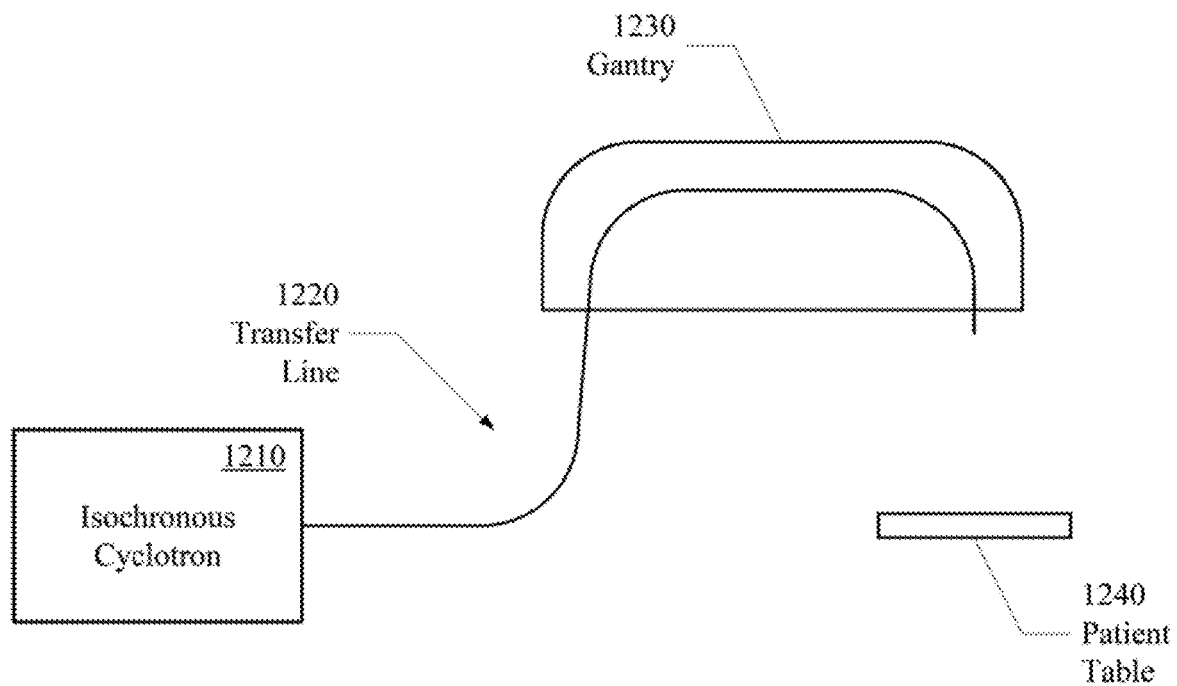
FIG. 12 shows an exemplary particle therapy system, in accordance with aspects of the present technology.

Referring now to FIG. 12, an exemplary particle therapy system, in accordance with aspects of the present technology, is shown. The particle therapy system 1200 can include an isochronous cyclotron 1210, a transfer line 1220, a gantry 1230 and a patient table 1240. The particle therapy system 1200 typically also includes numerous other components such as beam guiding components, beam scanning components, beam instrumentation components, vacuum components, power supply components, cooling components, mechanical support components, gantry drive components and the like, that are not necessary for an understanding of aspects of the present technology and therefore are not described further herein.

The isochronous cyclotron 1210 can be configured to generate a stream of protons in accordance with aspects of the present technology described above with regard to FIGS. 7A-7B, 8A-8B, 9, 10 and 11. The stream of protons can be output from the isochronous cyclotron 1210 onto the transfer line 1220. The gantry 1230 can be configured to rotate around the patient table 1240 to provide the charged particles to a target area, such a cancer or tumor in a patient. By rotating the gantry 1230 around the patient on the patient table 1240, a given dose can be delivered to the target area while reducing the dose delivered to surrounding tissue. Commonly the gantry 1230 can be configured to rotate by 180° about the patient table 1040.

The particle therapy system is just one possible application of the isochronous cyclotron in accordance with aspects of the present technology. Other possible applications can include nuclear magnetic resonance (NMR), magnetic resonance imaging (MRI), accelerator magnets for high energy physics (HEP) research, and nuclear fusion system.

Aspects of the present technology can advantageously provide an increased axial focusing component of the magnetic field in isochronous cyclotrons. Therefore, the average flux density of the radial increasing magnetic field in the beam chamber can be increased. The increased average flux density of the radial increasing magnetic field can advantageously allow the size of the beam chamber and the isochronous cyclotron in general to be reduced. The bulk superconductor sectors are passive and do not require routing of current, as compared to superconductor coil wrapped sectors. The bulk superconductor shapes in the bulk superconductor sectors can also be readily manufactured using machining, like cutting and milling, or molding or the like techniques. Therefore, the increased axial focusing component can be provided by bulk superconducting sectors that can be relatively easy to manufacture and or produced at a lower cost compared to other techniques for increasing the axial focusing component of the magnetic field in isochronous cyclotrons.

The following examples pertain to specific technology embodiments and point out specific features, elements, or steps that may be used or otherwise combined in achieving such embodiments.

Example 1 includes an isochronous cyclotron comprising: a beam chamber including a central axis and a median acceleration plane; a particle source coupled to the median acceleration plane proximate the central axis of the beam chamber; one or more coils disposed about the beam chamber; one or more radio frequency drive circuits coupled to the beam chamber; and a plurality of pairs of bulk superconductor sectors, wherein each pair of bulk superconductor sectors are disposed on opposite sides of the median acceleration plane.

Example 2 includes the isochronous cyclotron according to Example 1, further comprising: a plurality of pairs of structural sectors, wherein each pair of structural sectors are disposed on opposite sides of the median acceleration plane; and wherein the plurality of pairs of bulk superconductor sectors are disposed between adjacent pairs of structural sectors.

Example 3 includes the isochronous cyclotron according to Example 2, wherein the plurality of pairs of structural sectors comprise a plurality of pairs of magnetically neutral sectors.

Example 4 includes the isochronous cyclotron according to Example 2, wherein the plurality of pairs of structural sectors comprise a plurality of pairs of ferromagnetic, paramagnetic, or diamagnetic sectors.

Example 5 includes the isochronous cyclotron according to Example 1, wherein the plurality of pairs of bulk superconductor sectors include a bulk high-temperature superconductor.

Example 6 includes the isochronous cyclotron according to anyone of Examples 1 or 5, wherein the plurality of pairs of bulk superconductor sectors include a bulk type-II superconductor.

Example 7 includes the isochronous cyclotron according to Example 1, wherein the one or more coils comprise a pair of coils encircling the beam chamber and disposed on opposite sides of the median acceleration plane of the beam chamber.

Example 8 includes the isochronous cyclotron according to Examples 1 or 7, wherein the one or more coils comprise one or more superconductor coils.

Example 9 includes the isochronous cyclotron according to any one of Examples 1, 5 or 6, wherein the plurality of pairs of bulk superconductor sectors have a wedge shape.

Example 10 includes the isochronous cyclotron according to any one of Examples 1, 5 or 6, wherein the plurality of pairs of bulk superconductor sectors have a spiral shape.

Example 11 includes an isochronous cyclotron comprising: one or more coils disposed about a beam chamber and configured to generate a magnetic field in the beam chamber having a magnetic flux density that increases radially from a central axis of the beam chamber and is orientated substantially perpendicular to a median acceleration plane; and a plurality of pairs of bulk superconductor sectors, wherein each pair of bulk superconductor sectors are disposed on opposite sides of a median acceleration plane, and wherein the plurality of pairs of bulk superconductor sectors are configured to guide or concentrate the magnetic field to provide an axial focusing component of the magnetic field.

Example 12 includes the isochronous cyclotron according to Example 11, further comprising: a plurality of pairs of structural sectors, wherein each pair of structural sectors are disposed on opposite sides of the median acceleration plane of the beam chamber, and wherein the plurality of pairs of bulk superconductor sectors are disposed between adjacent pairs of structural sectors, and wherein the plurality of pairs of bulk superconductor sectors are configured to guide or concentrate the magnetic field into the beam chamber proximate the plurality of pairs of structural sectors.

Example 13 includes the isochronous cyclotron according to Example 12, wherein the plurality of pairs of structural sectors and the plurality of pairs of bulk superconductor sectors have a form factor configured to increase the axial focusing component of the magnetic field.

Example 14 includes the isochronous cyclotron according to Example 12, wherein an axial separation between respective pairs of the bulk superconductor sectors is smaller and or greater than an axial separation between respective pairs of the structural sectors.

Example 15 includes the isochronous cyclotron according to any one of Examples 11-14, wherein the plurality of pairs of bulk superconductor sectors include a bulk high-temperature superconductor.

Example 16 includes the isochronous cyclotron according to any one of Examples 11-14, wherein the plurality of pairs of bulk superconductor sectors include a bulk type-II superconductor.

Example 17 includes the isochronous cyclotron according to any one of Examples 11-14, wherein the plurality of pairs of bulk superconductor sectors are maintained in a mixed state.

Example 18 includes the isochronous cyclotron according to any one of Examples 11-14, wherein the one or more coils comprise a pair of coils encircling the beam chamber and disposed on opposite sides of the median acceleration plane of the beam chamber.

Example 19 includes the isochronous cyclotron according to any one of Examples 11-14, wherein the one or more coils comprise one or more superconductor coils.

Example 20 includes a charged particle acceleration method comprising: providing a plurality of pairs of bulk superconductor sectors, wherein each pair of bulk superconductor sectors are disposed on opposite sides of a median acceleration plane of a beam chamber, and wherein pairs of the bulk superconductor sectors are spaced apart from each other along a radial arch of the beam chamber; and providing a magnetic field in the beam chamber having a magnetic flux density that increases radially from a central axis of the beam chamber and is orientated substantially perpendicular to the median acceleration plane, wherein the plurality of pairs of bulk superconductor sectors are configured to guide or concentrate the magnetic field between the plurality of pairs of bulk superconductor sectors.

Example 21 includes the charged particle acceleration method of Example 20, further comprising:

providing a plurality of pairs of structural sectors, wherein each pair of structural sectors are disposed on opposite sides of the median acceleration plan of the beam chamber and wherein pairs of the bulk superconductor sectors are disposed between adjacent pairs of the structural sectors.

Example 22 includes the charged particle acceleration method of Example 20, further comprising: providing charge particles proximate a central axis of the beam chamber; and providing a radio frequency signal configured to accelerate the charged particles in the beam chamber in an orbital trajectory expanding outward from the central axis of the beam chamber.

Example 23 includes the charged particle acceleration method of any one of Examples 20-22, wherein the plurality of pairs of bulk superconductor sectors include a bulk high-temperature superconductor.

Example 24 includes the charged particle acceleration method of any one of Examples 20-22, wherein the plurality of pairs of bulk superconductor sectors include a bulk type-II superconductor.

Example 25 includes the charged particle acceleration method of any one of Examples 20-22, wherein the provided magnetic field is above a lower critical magnetic field $Hc_1$ and below an upper critical magnetic field $Hc_2$ of a bulk superconductor material of the bulk superconductor sectors.

The foregoing descriptions of specific embodiments of the present technology have been presented for purposes of illustration and description. They are not intended to be exhaustive or to limit the present technology to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is intended that the scope of the invention be defined by the claims appended hereto and their equivalents.

What is claimed is:

1. An isochronous cyclotron comprising:
   a beam chamber including a central axis and a median acceleration plane;
   a particle source coupled to the median acceleration plane proximate the central axis of the beam chamber;
   one or more coils disposed about the beam chamber;
   one or more radio frequency drive circuits coupled to the beam chamber; and
   a plurality of pairs of bulk superconductor sectors, wherein each pair of bulk superconductor sectors are disposed on opposite sides of the median acceleration plane and extend from the central axis along a radial length of the median acceleration plane.

2. The isochronous cyclotron according to claim 1, further comprising:
   a plurality of pairs of structural sectors, wherein each pair of structural sectors are disposed on opposite sides of the median acceleration plane; and
   wherein the plurality of pairs of bulk superconductor sectors are disposed between adjacent pairs of structural sectors.

3. The isochronous cyclotron according to claim 2, wherein the plurality of pairs of structural sectors comprise a plurality of pairs of magnetically neutral sectors.

4. The isochronous cyclotron according to claim 2, wherein the plurality of pairs of structural sectors comprise a plurality of pairs of ferromagnetic, paramagnetic, or diamagnetic sectors.

5. The isochronous cyclotron according to claim 1, wherein the plurality of pairs of bulk superconductor sectors include a bulk high-temperature superconductor.

6. The isochronous cyclotron according to claim 1, wherein the plurality of pairs of bulk superconductor sectors include a bulk type-II superconductor.

7. The isochronous cyclotron according to claim 1, wherein the one or more coils comprise a pair of coils encircling the beam chamber and disposed on opposite sides of the median acceleration plane of the beam chamber.

8. The isochronous cyclotron according to claim 1, wherein the one or more coils comprise one or more superconductor coils.

9. The isochronous cyclotron according to claim 1, wherein the plurality of pairs of bulk superconductor sectors have a wedge shape.

10. The isochronous cyclotron according to claim 1, wherein the plurality of pairs of bulk superconductor sectors have a spiral shape.

11. An isochronous cyclotron comprising:
    one or more coils disposed about a beam chamber and configured to generate a magnetic field in the beam chamber having a magnetic flux density that increases radially from a central axis of the beam chamber and is orientated substantially perpendicular to a median acceleration plane; and
    a plurality of pairs of bulk superconductor sectors, wherein each pair of bulk superconductor sectors are disposed on opposite sides of a median acceleration plane from the central axis to an outer extent of the median acceleration plane, and wherein the plurality of pairs of bulk superconductor sectors are configured to guide or concentrate the magnetic field to provide an axial focusing component of the magnetic field.

12. The isochronous cyclotron according to claim 11, further comprising:

a plurality of pairs of structural sectors, wherein each pair of structural sectors are disposed on opposite sides of the median acceleration plane of the beam chamber; and wherein the plurality of pairs of bulk superconductor sectors are disposed between adjacent pairs of structural sectors, and wherein the plurality of pairs of bulk superconductor sectors are configured to guide or concentrate the magnetic field into the beam chamber proximate the plurality of pairs of structural sectors.

13. The isochronous cyclotron according to claim 12, wherein the plurality of pairs of structural sectors and the plurality of pairs of bulk superconductor sectors have a form factor configured to increase the axial focusing component of the magnetic field.

14. The isochronous cyclotron according to claim 12, wherein an axial separation between respective pairs of the bulk superconductor sectors is smaller and or greater than an axial separation between respective pairs of the structural sectors.

15. The isochronous cyclotron according to claim 11, wherein the plurality of pairs of bulk superconductor sectors include a bulk high-temperature superconductor.

16. The isochronous cyclotron according to claim 11, wherein the plurality of pairs of bulk superconductor sectors include a bulk type-II superconductor.

17. The isochronous cyclotron according to claim 11, wherein the plurality of pairs of bulk superconductor sectors are maintained in a mixed state.

18. The isochronous cyclotron according to claim 11, wherein the one or more coils comprise a pair of coils encircling the beam chamber and disposed on opposite sides of the median acceleration plane of the beam chamber.

19. The isochronous cyclotron according to claim 11, wherein the one or more coils comprise one or more superconductor coils.

20. A charged particle acceleration method comprising:
providing a plurality of pairs of bulk superconductor sectors, wherein each pair of bulk superconductor sectors are disposed on opposite sides of a median acceleration plane of a beam chamber and extend a radial length of the median acceleration plane, and wherein pairs of the bulk superconductor sectors are spaced apart from each other along a radial arch of the beam chamber; and providing a magnetic field in the beam chamber having a magnetic flux density that increases radially from a central axis of the beam chamber and is orientated substantially perpendicular to the median acceleration plane, wherein the plurality of pairs of bulk superconductor sectors are configured to guide or concentrate the magnetic field between the plurality of pairs of bulk superconductor sectors to provide an axial focusing component of the magnetic field.

21. The charged particle acceleration method of claim 20, further comprising:
providing a plurality of pairs of structural sectors, wherein each pair of structural sectors are disposed on opposite sides of the median acceleration plan of the beam chamber and wherein pairs of the bulk superconductor sectors are disposed between adjacent pairs of the structural sectors.

22. The charged particle acceleration method of claim 20, further comprising:
providing charge particles proximate a central axis of the beam chamber; and
providing a radio frequency signal configured to accelerate the charged particles in the beam chamber in an orbital trajectory expanding outward from the central axis of the beam chamber.

23. The charged particle acceleration method of claim 20, wherein the plurality of pairs of bulk superconductor sectors include a bulk high-temperature superconductor.

24. The charged particle acceleration method of claim 20, wherein the plurality of pairs of bulk superconductor sectors include a bulk type-II superconductor.

25. The charged particle acceleration method of claim 20, wherein the provided magnetic field is above a lower critical magnetic field $Hc_1$ and below an upper critical magnetic field $Hc_2$ of a bulk superconductor material of the bulk superconductor sectors.

* * * * *